United States Patent [19]

Domke et al.

[11] Patent Number: 5,215,740

[45] Date of Patent: Jun. 1, 1993

[54] BUFFERING SYSTEM FOR ANTICALCULUS DENTIFRICES

[75] Inventors: Todd W. Domke, Newtown, Pa.; John P. Hauschild, Bridgewater, N.J.

[73] Assignee: Church & Dwight Co., Inc., Princeton, N.J.

[21] Appl. No.: 782,569

[22] Filed: Oct. 25, 1991

[51] Int. Cl.$^5$ .......................... A61K 7/16; A61K 7/18; A61K 33/10

[52] U.S. Cl. ........................................ 424/52; 424/49; 424/57; 424/717

[58] Field of Search ................................ 424/49–58, 424/717

[56] References Cited

U.S. PATENT DOCUMENTS

| | | |
|---|---|---|
| 3,927,202 | 12/1975 | Haruly et al. ................... 424/57 |
| 3,937,804 | 2/1976 | Delaney et al. .................. 424/52 |
| 4,024,237 | 5/1977 | Richel et al. .................... 424/53 |
| 4,174,387 | 11/1979 | Cordon et al. .................. 424/52 |
| 4,610,873 | 9/1986 | Rudy et al. ..................... 424/52 |
| 4,623,536 | 11/1986 | Winston et al. ................. 424/52 |
| 4,721,614 | 1/1988 | Winston et al. ................. 424/52 |
| 4,837,008 | 6/1989 | Rudy et al. ..................... 424/717 |
| 4,891,211 | 1/1990 | Winston .......................... 424/53 |
| 4,971,782 | 11/1990 | Rudy et al. ..................... 424/613 |
| 5,089,254 | 2/1992 | Coulson ........................... 424/57 |

FOREIGN PATENT DOCUMENTS

| | | | |
|---|---|---|---|
| 1027483 | 5/1978 | Canada .............................. | 424/57 |
| 1145677 | 5/1983 | Canada . | |
| 143757 | 9/1980 | Fed. Rep. of Germany ........ | 424/57 |
| 3543394 | 6/1987 | Fed. Rep. of Germany ........ | 424/57 |
| 1045691 | 10/1966 | United Kingdom ................. | 424/57 |
| 2188548 | 10/1987 | United Kingdom ................. | 424/57 |

*Primary Examiner*—Shep K. Rose
*Attorney, Agent, or Firm*—Bryan Cave

[57] ABSTRACT

A dentifrice for inhibiting calculus formation, comprising sodium bicarbonate, one or more alkali metal pyrophosphate salts, a soluble fluoride ion source and other adjuvants, in admixture with a buffering agent selected from among an alkali metal orthophosphate, o-phosphoric acid, an alkali metal glycerophosphate, tri(hydroxymethyl)aminomethane, tartaric acid or citric acid. The buffering agent is incorporated in the dentifrice in an amount of from about 0.1 to 2.5% by weight, sufficient to buffer the pH of the dentifrice to a value within the range of from about pH 8.2 to 8.9. The thus buffered dentifrice is subject to decreased risk of irritation of the oral mucosa or desquamation, as compared with dentifrices excluding such a buffering agent.

10 Claims, No Drawings

BUFFERING SYSTEM FOR ANTICALCULUS DENTIFRICES

TECHNICAL FIELD

The present invention relates to anticalculus dentifrices, in particular, toothpastes, gels or liquids, which contain sodium bicarbonate and calculus-inhibiting amounts of one or more alkali metal pyrophosphate salts and soluble fluoride ion sources.

BACKGROUND OF THE INVENTION

In recent years a number of dentifrices have been proposed for inhibiting the formation of calculus, or tartar as it is also referred to, on tooth surfaces. In particular, the patent literature contains numerous disclosures of dentifrices containing mixtures of various alkali metal pyrophosphate salts and soluble fluorides as anticalculus agents. Such disclosures appear, for example, in Parran et al U.S. Pat. Nos. 4,515,772, 4,590,066, 4,684,518, 4,806,339, 4,885,155 and 4,999,184; and in Gaffar et al U.S. Pat. Nos. 4,627,977, 4,806,340, 4,806,342, 4,869,898, 4,889,712, 4,906,456, 4,925654, 4,931,273 and 4,966,777.

More recently, in copending application Ser. No. 573,340 filed Aug. 30, 1991, entitled "Anticalculus Dentifrices" and owned by the assignee of the present invention, it has been disclosed that the addition of sodium bicarbonate to an alkali metal pyrophosphate/soluble fluoride-containing, anticalculus dentifrice imparts improved calculus-inhibiting properties thereto. The disclosure of that application is incorporated by reference herein.

It has been found that anticalculus toothpastes and gels and liquids incorporating both sodium bicarbonate and alkali metal pyrophosphate/soluble fluoride mixtures possess neat pH values (i.e., pH values of the toothpaste or gel prior to application and dilution with saliva) in the range of from about 9.0 to 9.6. Dentifrices which are so alkaline may be irritating to the oral mucosa. Accordingly, it is a principal object of the present invention to provide a buffering system for the sodium bicarbonate-alkali metal pyrophosphate/soluble fluoride anticalculus toothpastes or gels described in the aforesaid copending application. Other objects and advantages of the present invention will be apparent from the following description of preferred embodiments thereof.

SUMMARY OF THE INVENTION

In accordance with the present invention, a buffering system is provided for anticalculus toothpaste, gel and liquid dentifrices which comprise at least about 8% by weight of sodium bicarbonate, from about 1 to 10% by weight of one or more alkali metal pyrophosphate salts and a soluble fluoride ion source incorporated in the dentifrice in an amount sufficient to supply from about 25 to 5,000 ppm fluoride ion. The buffering system thus incorporated in the dentifrice comprises a buffering agent selected from among the alkali metal orthophosphates,o-phosphoric acid, tris(hydroxymethyl)aminomethane [also known as Tris or Tromethamine], an alkali metal glycerophosphate salt, tartaric acid or citric acid. The buffering agent is incorporated in the dentifrice in an amount of from about 0.1 to 2.5% by weight of the dentifrice, that amount being sufficient to buffer the pH of the dentifrice to a value within the range of from about 8.2 to 8.9.

Sodium bicarbonate-pyrophosphate/soluble fluoride anticalculus dentifrices containing the buffering system of the invention exhibit excellent anticalculus properties with decreased risk of oral mucosal irritation or desquamation, as compared with dentifrices which omit such buffering system.

It has been found that, absent the provision of the buffering system of the invention, the neat pH of sodium bicarbonate-pyrophosphate/soluble fluoride anticalculus toothpastes or gel dentifrices cannot be readily reduced below about pH 9.0. Even di-alkali metal pyrophosphates (such as $Na_2H_2P_2O_7$), conventional buffers for pyrophosphate-containing anticalculus dentifrices, are ineffective to reduce the pH of such dentifrices containing sodium bicarbonate below about pH 9.0 (see Controls C-E below). This is believed attributable to the fact that, in the presence of high concentrations of sodium bicarbonate only small proportions of the di-alkali metal pyrophosphates dissolve, thus minimizing any buffering effect thereof.

The buffering agents useful in the dentifrice of the present invention are, on the other hand, soluble in the liquid phase of the toothpaste or gel. The preferred buffering agents which may be so utilized are the sodium and potassium orthophosphates, desirably the sodium salts such as monosodium dihydrogen orthophosphate, alone or in admixture with disodium hydrogen orthophosphate. As noted above, the buffering agents are suitably incorporated in the dentifrice in amounts of from about 0.1 to 2.5%, preferably from about 0.25 to 1.5%, by weight thereof, these amounts being sufficient to buffer the pH of the neat dentifrice to a value within the range of from about pH 8.2 to 8.9, preferably from about pH 8.4 to 8.8, respectively.

The use of phosphate buffers, including mixtures of monobasic and dibasic sodium phosphates, has long been known for preparing buffer solutions having pH values of from about pH 5.8 to 7.8. The use of tris(hydroxymethyl)aminomethane is also well-known. However, the use of either these materials or the alternative buffering agents described above for buffering sodium bicarbonate-pyrophosphate/soluble fluoride dentifrices to values within the range of from about pH 8.2 to 8.9 to minimize the risk of irritation to the oral mucosa has not, to our knowledge, previously been disclosed or suggested in the literature.

The other constituents of the anticalculus dentifrice formulations of the invention correspond to those described in the aforesaid copending application. Thus, sodium bicarbonate (baking soda) is incorporated in the dentifrice as both an anticalculus adjuvant and an abrasive. Desirably, the sodium bicarbonate particles have a mean particle size within the range of about $5\mu$ to $200\mu$, preferably about $20\mu$ to $120\mu$, in diameter. The bicarbonate particles may be incorporated in the dentifrice in varying amounts, so long as it is present in an amount effective to impart the desired abrasive characteristics and to promote inhibition of calculus formation when the dentifrice is applied to the teeth. Accordingly, as used herein, the term "effective" or "effective amount" means a sufficient amount of the ingredient being utilized to provide the desired effect or result. Preferably, the amount of sodium bicarbonate required to impart both abrasive and anticalculus adjuvant effects is from about 8% to as much as about 65% by weight for a typical toothpaste or gel formulation. At lower concentrations of bicarbonate the enhancement of anticalculus activity will be small. However, with a concentration of sodium bicarbonate even as low as 8% and a water content of less than about 30%, the noticeable presence of high proportions of gritty tetrasodium pyrophosphate particles will be avoided.

The soluble pyrophosphate salts which may be incorporated in the dentifrice include mono-, di-, tri- or tetra-alkali metal pyrophosphates and mixtures thereof. The Preferred pyrophosphate salts include disodium pyrophosphate, tetrasodium pyrophosphate, tetrapotassium pyrophosphate, and mixtures thereof. The pyrophosphates may be employed in their anhydrous as well as their hydrated forms. Although a particular pyrophosphate salt, e.g., disodium pyrophosphate, may be the pyrophosphate initially added to the formulation, the actual pyrophosphate and the quantity present in the product is dependent on both the final pH of the formulation and the salting-out effect of the sodium bicarbonate.

The preferred dentifrice formulations, which contain about 20 to 60% sodium bicarbonate and possess pH values of about 7.5 to 9.5, contain no more than about 1.5%, typically about 0.4–10%, of dissolved pyrophosphate ions, primarily in the form of $HP_2O_7^{-3}$ and $P_2O_7^{-4}$ ions. The balance of the pyrophosphate salt content, e.g. in amounts of about 1.5 to 13.5% by weight of the dentifrice, is in the form of undissolved tetrasodium pyrophosphate decahydrate salted-out by the sodium bicarbonate.

As further indicated, the dentifrice also includes a water-soluble fluoride ion source which is effective both as a pyrophosphatase inhibitor and as an anti-caries agent. Fluoride ion sources thus useful include inorganic fluoride salts, such as soluble alkali metal or alkaline earth metal salts, for example, sodium fluoride, potassium fluoride, sodium fluosilicate, ammonium fluosilicate, sodium fluozirconate or sodium monofluorophosphate. Alkali metal fluorides such as sodium fluoride, or sodium monofluorophosphate, and mixtures thereof, are preferred.

The amount of the soluble fluoride ion source in the dentifrice is dependent on the particular compounds used, but it must be incorporated in an effective but nontoxic amount, generally up to about 5.0% of the preparation. Any suitable minimum amount of such compound may be used, but it is preferable to employ a sufficient quantity as to release about 25 up to a maximum of 5,000 ppm, preferably about 850 to 1500 ppm. of fluoride ion. Typically, in the case of sodium fluoride the fluoride ion source is present in an amount from 0.05% to 0.65% by weight, based on the weight of the dentifrice, and preferably in the range of 0.18% to about 0.35%. In the case of sodium monofluorophosphate the compound may be present in an amount of about 0.2-2%, more typically from about 0.65%–1.20%.

The toothpaste or gel vehicle may also contain, if desired, a conventional abrasive or polishing material, in addition to the sodium bicarbonate. Conventional water-insoluble abrasives which are so useful include sodium metaphosphate, potassium metaphosphate, tricalcium phosphate, calcium phosphate dihydrate, anhydrous dicalcium phosphate, calcium pyrophosphate, magnesium orthophosphate, trimagnesium phosphate, calcium carbonate, aluminum silicate, zirconium silicate, hydrated silica, hydrated alumina, bentonite, and mixtures thereof.

Preferred abrasive materials which may be admixed with the sodium bicarbonate include hydrated silica, silica gel or colloidal silica, and complex amorphous alkali metal aluminosilicates. When visually clear gels are employed, polishing agents of hydrated or colloidal silica, alkali metal aluminosilicate complexes and alumina are particularly useful, since they have refractive indices close to the refractive indices of gelling agent-liquid (including water and/or humectant) systems commonly used in such dentifrices.

Any of the foregoing water-insoluble abrasives may be present as an adjunct or secondary abrasive in concentrations of up to about 50%, preferably, in amounts up to about 20%, by weight of the dentifrice.

Organic surface-active agents are used in the dentifrices of the present invention to achieve increased cleaning action, assist in achieving thorough and complete dispersion of the anticalculus agent throughout the oral cavity, and improve the detergent and foaming properties of the dentifrices. Organic surfactants which may be so utilized can be anionic, nonionic or ampholytic in nature.

Examples of suitable anionic surfactants are water-soluble salts of the higher alkyl sulfates, such as sodium lauryl sulfate or other suitable alkyl sulfates having 8 to 18 carbon atoms in the alkyl group, water-soluble salts of higher fatty acid monoglyceride monosulfates, such as the sodium salt of the monosulfated monoglyceride of hydrogenated coconut oil fatty acids, alkyl aryl sulfonates such as sodium dodecyl benzene sulfonate, higher alkyl sulfoacetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosinate, and the sodium, potassium, and ethanolamine salts of N-lauroyl, N-myristoyl, or N-palmitoyl sarcosinate which should be substantially free from soap or similar higher fatty acid materials.

Other suitable surface-active materials include nonionic agents such as condensates of sorbitan monostearate with ethylene oxide, condensates of ethylene oxide with propylene oxide or, condensates of propylene glycol (available under the trademark "Pluronics"). Other examples of water-soluble nonionic surfactants useful in the dentifrice of the present invention are the condensation products of ethylene oxide with various other compounds which are reactive therewith and have long hydrophobic chains (e.g. aliphatic chains of about 12 to 20 carbon atoms), which condensation products ("ethoxamers") contain hydrophilic polyoxyethylene moieties, such as condensation products of poly-(ethylene oxide) with fatty acids, fatty alcohols, fatty amides, or polyhydric alcohols (e.g., sorbitan monostearate).

The various surfactants may be utilized alone, or in admixture with one another. In toothpastes, for example, the aggregate amount of the surfactant or surfactants used is preferably within the range of about 0.05% to about 5%, more preferably, from about 0.1% to about 1.0%, by weight.

Suitable flavoring and sweetening agents may also be employed in the dentifrice of the invention. Examples of suitable flavorants include the flavoring oils, for example, oils of spearmint, peppermint, wintergreen, sassafras, clove, sage, eucalyptus, marjoram, cinnamon, lemon and orange, as well as methylsalicylate. Suitable sweeteners include sodium cyclamate, perillartine, saccharin, sodium saccharin and ammoniated glycyrrhizin (e.g., its monoammonium salt), and the like. Suitably, the flavoring and sweetening agent together comprise from about 0.01% to 5% or more by weight of the dentifrice. Preferably, the amount of flavoring oil is above 0.3%, e.g. 0.8 to 1.2%.

Various other materials may be incorporated in the dentifrice of this invention. Examples thereof are coloring and whitening agents, preservatives, silicones, chlorophyll compounds, and mixtures thereof, and other constituents. These adjuvants are incorporated in the instant compositions in amounts which do not substantially adversely affect the properties and characteristics desired and are selected and used in effective amounts, depending upon the particular adjuvant and type of preparation involved.

In a toothpaste, the liquid vehicle may comprise water and humectant, typically in an amount ranging from about 10% to about 90% by weight of the preparation. Glycerine, propylene glycol, sorbitol, polypropylene glycol and/or polyethylene glycol (e.g., molecular weight of 400–600) exemplify suitable humectants/carriers. Also advantageous are liquid mixtures of water, glycerine and sorbitol. In translucent gels, where the refractive index is an important consideration, it is preferred to use higher ratios of humectant to water than in opaque pastes.

Toothpastes and gels typically also contain a natural or synthetic thickener or gelling agent in proportions of about 0.1% to about 10%, preferably about 0.5% to about 5%, by weight. Suitable organic thickeners include sodium carboxymethyl cellulose, gum tragacanth, starch, carrageenan, polyvinylpyrrolidone, hydroxyethylpropyl cellulose, hydroxybutyl methyl cellulose, hydroxypropyl methyl cellulose, or hydroxyethyl cellulose, and are usually used in concentrations of 0.1–2.0%. Inorganic thickeners such as hydrated silicas may also be used at levels of about 0.5–10%.

It is particularly preferred to incorporate the following ingredients in the buffered sodium bicarbonate-pyrophosphate/soluble fluoride ion, calculus inhibiting tooth pastes or gels of the invention:

| Ingredient | Amounts, Percent by Weight (Unless Otherwise Indicated) | |
| --- | --- | --- |
| | Broad Range | Preferred Range |
| Toothpastes or Dental Creams | | |
| Sodium Bicarbonate | 20.00 to 65.00 | 30.00 to 60.00 |
| Pyrophosphate Salt | 2.50 to 15.00 | 2.50 to 5.00 |
| Humectant | 5.00 to 60.00 | 10.00 to 35.00 |
| Organic Thickener | 1.00 to 2.00 | 0.30 to 1.50 |
| Inorganic Thickener | 0.00 to 10.00 | 0.00 to 5.00 |
| Surfactant | 0.05 to 5.00 | 0.10 to 1.00 |
| Water Insoluble Abrasive | 0.00 to 50.00 | 0.00 to 20.00 |
| Sweetener | 0.00 to 10.00 | 0.30 to 2.00 |
| Fluoridating Agent as fluoride ion | 25.00 to 5000 ppm | 850 to 1500 ppm |
| Flavoring Agent | 0.01 to 5.00 | 0.30 to 2.00 |
| Buffering Agent | 0.1 to 2.50 | 0.25 to 2.50 |
| Water | 3.00 to 60.00 | 5.00 to 35.00 |
| Dental Gels | | |
| Sodium Bicarbonate | 20.00 to 60.00 | 20.00 to 40.00 |
| Pyrophosphate Salt | 2.50 to 15.00 | 2.50 to 5.00 |
| Humectant | 10.00 to 60.00 | 10.00 to 50.00 |
| Organic Thickener | 0.10 to 2.00 | 0.30 to 1.50 |
| Inorganic Thickener | 0.00 to 10.00 | 3.00 to 8.00 |
| Surfactant | 0.00 to 10.00 | 0.30 to 1.00 |
| Water Insoluble Abrasive | 0.00 to 50.00 | 0.00 to 20.00 |
| Sweetener | 0.00 to 10.00 | 0.30 to 2.00 |
| Fluoridating Agent as fluoride ion | 25.00 to 5000 ppm | 850 to 1500 ppm |
| Flavoring Agent | 0.01 to 5.00 | 0.30 to 2.00 |
| Buffering Agent | 0.10 to 2.50 | 0.25 to 2.50 |
| Water | 3.00 to 30.00 | 5.00 to 20.00 |

In accordance with a further feature of the present invention, the buffered dentifrice compositions hereof prepared by initially admixing the pyrophosphate salt(s), the soluble fluoride ion source, the buffering system and any additional adjuvants, prior to the addition of the sodium bicarbonate thereto. On the other hand, it has been found that if the bicarbonate is added to the dentifrice formulation prior to the buffering agent, the efficacy of the buffering system is partially lost. It is believed that such decrease in effect is due to reaction of the acidic species in the formulations with the bicarbonate to form water and carbon dioxide.

In addition, prior to the addition of the bicarbonate ingredient, the pH of the mixture of the pyrophosphate(s), the fluoride ion source, the buffering system and any further adjuvants should be established at a value within the range of about pH 8 to 8.2, in order to minimize reaction with the bicarbonate subsequently added. When, for example, the formulation contains relatively large proportions of di-alkali metal pyrophosphates, the pH of the mixture formed prior to the addition of the bicarbonate may be below 7. It has been found that formulations having such relatively low pH values are subject to the loss of bicarbonate during processing, which loss may be substantially and pose processing difficulties in large-scale commercial manufacture because of the build-up of carbon dioxide. Accordingly, it is desirable to establish and maintain the pH of the mixture prior to addition of the bicarbonate at a value within the range of about pH 8 to 8.2, as aforesaid.

PREFERRED EMBODIMENTS OF THE INVENTION

The following examples illustrate preferred embodiments of the dentifrice of the present invention. All amounts and proportions referred to therein (and in the appended claims) are by weight, unless otherwise specified.

EXAMPLE I-IV

Four different toothpaste formulations (Examples I-IV) were prepared by initially mixing each of the ingredients (save for the sodium bicarbonate) under ambient conditions in the proportions specified in Table 1 below. Each of the formulations contained 3.5% pyrophosphate anion. Examples I, II and III demonstrate the use of monosodium dihydrogen phosphate along (Example I) or in admixture with disodium hydrogen phosphate (Examples II and III) as the buffering agent used in accordance with the invention. Example II shows that even a low amount of the phosphate buffering agent is effective in producing a dentifrice having a suitable pH value. Example IV is a formation incorporating the Tris buffer to provide a formulation having the requisite pH value.

For comparison, a number of control formulations (Controls A-E) were prepared in the same manner as Examples I-IV, without the addition of the buffering agent hereof. Controls A and B demonstrate that a sodium bicarbonate-containing dentifrice incorporating either tetrasodium or tetrapotassium pyrophosphate, but without the buffering agent, has a neat paste pH equal to or greater than pH 9. Controls C-E, on the other hand, demonstrate that the conventional use of a disodium pyrophosphate salt to buffer pyrophosphate-containing anticalculus dentifrices is also ineffective in reducing the neat paste pH of the baking soda-containing dentifrice below pH 9. The pH of Control C should be specifically compared to that of Example II. Controls D and E contain tetraalkali metal and dialkali metal pyrophosphate salts in the same proportions as utilized in the examples given in Parran et al U.S. Pat. No. 4,515,772.

The formulations of the respective example and control dentifrices are set forth in the following tables:

TABLE 1

| | EXAMPLES OF INVENTION PARTS BY WEIGHT | | | |
|---|---|---|---|---|
| INGREDIENT | EXAMPLE I | EXAMPLE II | EXAMPLE III | EXAMPLE IV |
| Glycerin | 14.07 | 11.03 | 14.07 | 14.00 |
| PEG-8 (Polyethylene Glycol) | 1.00 | 1.00 | 1.00 | 1.00 |
| Sodium Carboxymethylcellulose | 0.65 | 0.70 | 0.70 | 0.70 |
| Distilled Water | 19.22 | 19.22 | 20.18 | 18.00 |
| Sodium Fluoride | 0.24 | 0.24 | 0.24 | 0.24 |
| Monosodium Dihydrogen o-Phosphate | 0.75 | 0.14 | 0.03 | — |
| Disodium Hydrogen o-Phosphate | — | 0.11 | 0.72 | — |
| Tromethamine Base[1] | — | — | — | 1.00 |
| Hydrochloric Acid (50%) | — | — | — | 0.82 |
| Tetrapotassium Pyrophosphate | — | — | — | — |
| Tetrasodium Pyrophosphate | 5.35 | 5.35 | 5.35 | 5.35 |
| Disodium Dihydrogen Pyrophosphate | — | — | — | — |
| Sodium Saccharin | 1.21 | 1.00 | 1.00 | 1.00 |
| Sodium Bicarbonate | 55.30 | 59.00 | 54.50 | 55.68 |
| Sodium Lauryl Sulfate | 0.30 | 0.30 | 0.30 | 0.30 |
| Sodium Lauroyl Sarcosinate (30%) | 1.00 | 1.00 | 1.00 | 1.00 |
| Flavor | 0.91 | 0.91 | 0.91 | 0.91 |
| Total | 100.00 | 100.00 | 100.00 | 100.00 |
| Neat Paste pH | 8.7 | 8.6 | 8.7 | 8.6 |

[1]Tris(hydroxymethyl)Aminomethane

TABLE 2

| | PARTS BY WEIGHT | | | | |
|---|---|---|---|---|---|
| INGREDIENT | CONTROL A | CONTROL B | CONTROL C | CONTROL D | CONTROL E |
| Glycerin | 14.66 | 12.07 | 12.22 | 14.07 | 14.07 |
| PEG-8 | 1.00 | 1.00 | 1.00 | 1.00 | 1.00 |
| Sodium Carboxymethylcellulose | 0.95 | 0.80 | 0.80 | 0.65 | 0.65 |
| Distilled Water | 13.19 | 17.23 | 17.13 | 19.22 | 19.22 |
| Sodium Fluoride | 0.24 | 0.24 | 0.24 | 0.24 | 0.24 |
| Monosodium Dihydrogen o-Phosphate | — | — | — | — | — |
| Disodium Hydrogen o-Phosphate | — | — | — | — | — |
| Tromethamine Base[1] | — | — | — | — | — |
| Tetrapotassium Pyrophosphate | 6.65 | — | — | 1.58 | — |
| Tetrasodium Pyrophosphate | — | 5.35 | 5.00 | 2.52 | 3.81 |
| Disodium Dihydrogen Pyrophosphate | — | — | 0.30 | 1.25 | 1.54 |
| Sodium Saccharin | 1.00 | 1.00 | 1.00 | 1.21 | 1.21 |
| Sodium Bicarbonate | 60.00 | 60.00 | 60.00 | 56.05 | 56.05 |
| Sodium Lauryl Sulfate | 0.30 | 0.30 | 0.30 | 0.30 | 0.30 |
| Sodium Lauroyl Sarcosinate (30%) | 1.00 | 1.00 | 1.00 | 1.00 | 1.00 |
| Flavor | 1.01 | 1.01 | 1.01 | 0.91 | 0.91 |
| Neat Paste pH | 9.2 | 9.2 | 9.1 | 9.0 | 9.0 |

[1]Tris(Hydroxymethyl)Aminomethane

The foregoing description is intended as illustrative only. Thus, the hypothesis as to the improved efficacy of the buffering system of the invention achieved by incorporating the buffering agent in the dentifrice formulation prior to the addition of sodium bicarbonate, or by establishing the pH range of the mixtures prior to the addition of the bicarbonate within the range of about pH 8 to 8.2, are intended as explanatory only and not as limiting. Rather, the scope of the invention should be construed based on the claims appended hereto.

We claim:

1. In a toothpaste or gel dentifrice composition for inhibiting calculus formation, composing sodium bicarbonate as the principal abrasive and as an anticalculus adjuvant in the dentifrice in an amount of at least 20% by weight, from 1 to 10% by weight of one or more alkali metal pyrophosphate salts as an anticalculus agent and a soluble fluoride ion source in an amount sufficient to supply from 25 to 5,000 ppm fluoride ion, the improvement comprising incorporating an alkali metal orthophosphate as a buffering agent in the dentifrice, the buffering agent being incorporated in an amount of from 0.1 to 2.5% by weight of the dentifrice, sufficient to buffer the pH of the dentifrice to a value within the range of from pH 8.2 to 8.9.

2. The dentifrice of claim 1, in which the buffering agent is incorporated in an amount of from 0.25 to 2.5% by weight thereof, said amount being sufficient to buffer the pH of the dentifrice to a value within the range of from pH 8.4 to 8.8.

3. The dentifrice of claim 1, wherein the buffering agent is an alkali metal dihydrogen orthophosphate, alone or in admixture with a di-alkali metal hydrogen orthophosphate.

4. The dentifrice of claim 3, wherein the buffering agent is monosodium dihydrogen orthophosphate, alone or in admixture with disodium hydrogen orthophosphate.

5. A process for the preparation of a toothpaste or gel dentifrice composition for inhibiting calculus formation, which comprises:
    (a) admixing
        one or more alkali metal pyrophosphate salts useful in the dentifrice as an anticalculus agent, in an amount of from 1 to 10% by weight of the dentifrice,
        a soluble fluoride ion source, ion an amount sufficient to supply from 25 to 5,000 ppm of fluoride ion,
        an alkali metal orthophosphate useful in the dentifrice as a buffering agent, and
        an orally acceptable vehicle; and
    (b) adding sodium bicarbonate, useful in the dentifrice as the principal abrasive and as an anticalculus adjuvant, to the resulting mixture in an amount of at least 20% by weight of the dentifrice;
        the amount of the buffering agent being sufficient to buffer the pH of the dentifrice to a value within the range of pH 8.2 to 8.9.

6. The process of claim 5, wherein the pH of the mixture formed in step (a) is maintained at a value between pH 8 and 8.2 to minimize reaction of the acidic species thereof with the bicarbonate ion upon the addition of sodium bicarbonate in step (b).

7. A method for inhibiting the formation of dental calculus, which comprises applying to the teeth a toothpaste or gel dentifrice comprising, in an orally acceptable vehicle:
    (a) sodium bicarbonate as the principal abrasive and as an anticalculus adjuvant in the dentifrice, in an amount of at least 20% by weight of the dentifrice;
    (b) one or more alkali metal pyrophosphate salts as an anticalculus agent, in an amount of from 1 to 10% by weight of the dentifrice; and
    (c) a soluble fluoride ion source in an amount sufficient to supply from 25 to 5,000 ppm fluoride ion by weight of the dentifrice; and
    (d) an alkali metal orthophosphate as a buffering agent, in an amount of from 0.1 to 2.5% by weight of the dentifrice, the amount of the buffering agent being sufficient to buffer the pH of the dentifrice to a value within the range of from pH 8.2 to 8.9.

8. The method of claim 7, wherein the buffering agent is incorporated in the dentifrice in an amount of from 0.25 to 1.5% by weight thereof, such that the pH of the dentifrice is within the range of from pH 8.4 to 8.8.

9. The method of claim 7, wherein the buffering agent is an alkali metal dihydrogen orthophosphate, alone or in admixture with a di-alkali metal hydrogen orthophosphate.

10. The method of claim 7, wherein the buffering agent is monosodium dihydrogen phosphate, alone or in admixture with disodium hydrogen phosphate.

* * * * *

UNITED STATES PATENT AND TRADEMARK OFFICE
CERTIFICATE OF CORRECTION

PATENT NO. :  5,215,740

DATED      :  June 1, 1993

INVENTOR(S):  TODD W. DOMKE and JOHN P. HAUSCHILD

It is certified that error appears in the above-identified patent and that said Letters Patent is hereby corrected as shown below:

Column 9, line 10:  Delete "composing" and insert --comprising--.

Column 9, line 47:  Delete "ion and amount" and insert --in an amount--.

Column 10, line 27:  After "dentifrice;" delete "and".

Signed and Sealed this

Thirty-first Day of August, 1993

Attest:

BRUCE LEHMAN

Attesting Officer

Commissioner of Patents and Trademarks